United States Patent [19]

Masliyah

[11] Patent Number: 4,820,296
[45] Date of Patent: Apr. 11, 1989

[54] POST-OPERATIVE GARMENT

[76] Inventor: Carol A. Masliyah, 1206 Nautilus, La Jolla, Calif. 92037

[21] Appl. No.: 723,168

[22] Filed: Apr. 15, 1985

[51] Int. Cl.$^4$ .................................... A61F 13/16
[52] U.S. Cl. .................... 604/385.1; 604/394; 604/389
[58] Field of Search .............. 604/389, 385, 358, 394, 604/395, 390, 392, 397, 398, 402

[56] References Cited

U.S. PATENT DOCUMENTS

| | | | |
|---|---|---|---|
| 1,206,167 | 11/1916 | Swetzel | 604/392 |
| 2,714,889 | 8/1955 | Chambers | 604/390 |
| 3,431,908 | 3/1969 | Lee | 604/385 |
| 3,575,175 | 4/1971 | McGuire | 604/390 |
| 4,410,325 | 10/1983 | Lare | 604/389 |

FOREIGN PATENT DOCUMENTS 637813  11/1936  Fed. Rep. of Germany ...... 604/394

Primary Examiner—John D. Yasko
Attorney, Agent, or Firm—Ralph S. Branscomb

[57] ABSTRACT

A post-operative garment is provided for patients who have just been through lower abdominal, groin, or rectal operations such as Caesarean sections, hemorrhoidectomies, and hernia operations. The garment is somewhat diaper-like, having a soft, absorbent inner portion and an impermeable membrane on the outside. The garment passes through the crotch and expands laterally outwardly both front and rear, with the front and back being fastened to one another up above the abdominal region in the rib cage area. This eliminates the need for belts of the type that are used for sanitary napkins, which cut into the incision area, and also provides a greater degree of privacy for the patient as well as a greater degree of overall comfort.

4 Claims, 1 Drawing Sheet

POST-OPERATIVE GARMENT

BACKGROUND OF THE INVENTION

The invention was inspired by post-operative Caesarean section patients, although its utility expands to patients who have undergone a variety of operations in the lower region of the torso.

Currently, women who have experienced Caesarean sections have nothing to wear over the crotch to absorb discharges and blood other than sanitary napkins, which are held in place by the same sanitary belts that are used by non-post-operative women. The stretch material of the sanitary belt binds at the sensitive region where the incision was made, and is extremely uncomfortable and even painful. If it is tight enough to hold a sanitary napkin in place, it digs into the wound, especially as the patient moves, and contrary to providing a soothing, gentle feeling which the patient would appreciate, actually causes discomfort and pain.

The sanitary belt also allows for slipping of the pad and gives the wearer an insecure feeling. In addition to the insecurity caused by the frequent slipping of the pad, the sanitary belt and the pad provide such scant coverage that the patient, who ordinarily would be wearing a flimsy hospital gown, feels generally exposed in her lower abdominal region, to which she has an instinctive feeling of uneasiness and exposure.

When the Caesarean section patient tries to go the bathroom, the sanitary belt poses even further problems. The belt must be either slipped down or stepped out of. Then, the pad must be replaced by reaching through the legs to try to retread the pad through the pad fasteners. The difficulty of these motions undergone by the post-operative patients is exacerbated if the patient must move quickly, and is further aggravating when an intravenous pole must be taken to the restroom, so that the patient has limited mobility of one hand and arm. The patient must struggle to change the sanitary pad and do the best she can to avoid having the pad slip into the toilet bowl or on the floor.

SUMMARY OF THE INVENTION

The instant invention is similar in concept to a diaper, but it is critically dimensioned and shaped to resolve the above-stated problems in a number of different ways. The design of the protective-like garment eliminates binding and pulling at the incision areas completely by moving the fastening area up to the rib cage, just under the breasts in the case of the Caesarean section. Thus, no cutting or binding at all is experienced in the Caesarean incision area. The garment is completely disposable, and has either a built-in pad at the crotch, or a peel-off adhesive layer to which a sanitary napkin can be bonded. In addition to caesarian sections, the garment can be used after other operations such as hemorrhoidectomies, or for general use in which urine, blood, feces, or draining soilage must be absorbed and contained.

The design of the garment permits air to circulate to the body, and yet minimizes the feeling of exposure to the public that the wearer of a sanitary napkin belt experiences. Additionally, and very importantly, especially in the case of a Caesarean patient, there is a feeling of looseness or hollowness in the abdomen that is not very comfortable. The instant garment, by passing over and into contact with the abdominal region in a non-binding fashion, produces an ever so slight pressure against the abdomen that is non-invasive but just enough to be soothing and alleviate the feeling of hollowness and looseness in the abdominal cavity.

DETAILED DESCRIPTION OF THE PREFERRED EMBODIMENTS

Figure 1:
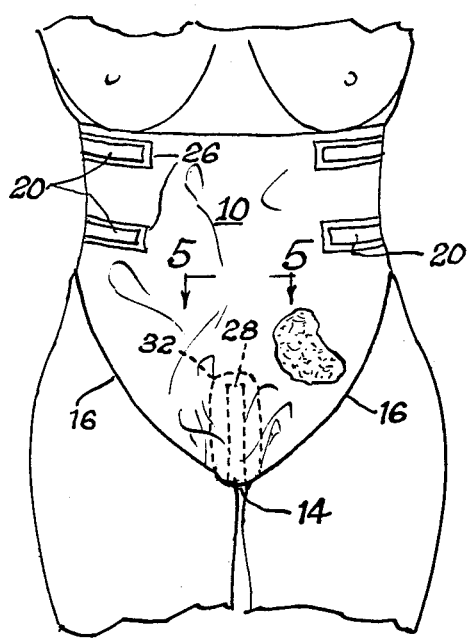
FIG. 1 is a front elevation view of the garment in use by a patient.
Figure 2:
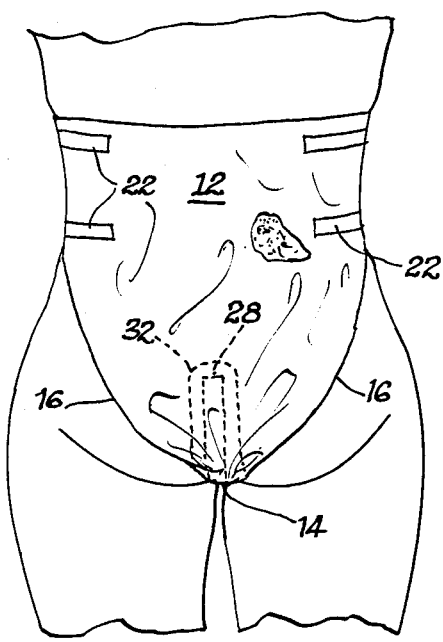
FIG. 2 is a rear elevation view of the garment in FIG. 1 as seen in the rear side of the patient.
Figure 3:
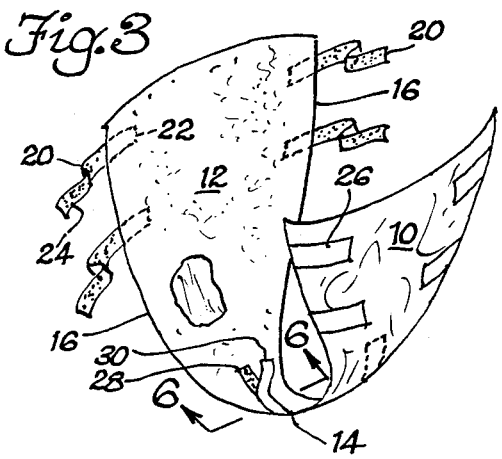
FIG. 3 is a perspective view of the garment off of the patient.

The invention is very simple in concept, and is similar to a diaper, although the results of the use of the garment, because of its specific design, are impressive. the first embodiment is shown in FIGS. 1–3. There is a front panel 10 and a rear panel 12. The front and rear panels are joined in the crotch area 14. Actually, it is more accurate to say that the garment is a single piece, which converges downward from the front panel into a crotch area and then expands rearwardly to define the rear panel.

Figure 4:
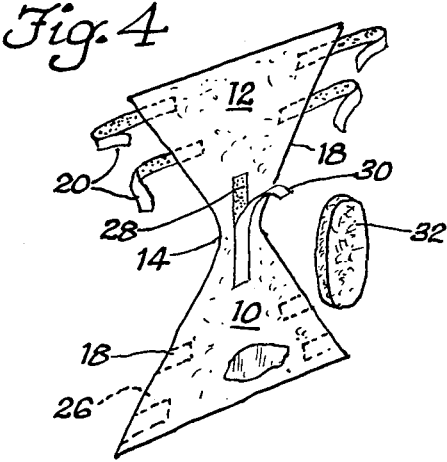
FIG. 4 is a perspective view of a slight modification of the garment's shape in which the front and back panels are generally triangular.
Figure 5:
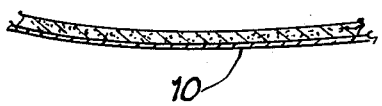
FIG. 5 is a section taken along line 5—5 of FIG. 1 illustrating the composition of the garment fabric.
Figure 6:
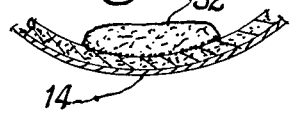
FIG. 6 is a section taken through line 6—6 of FIG. 3, illustrating one means of attaching a sanitary pad to the garment.

A modified shape of the garment is shown in FIG. 4. In FIGS. 1–3, the edges 16 of the garment are curved so that when the garment is laid out flat, it somewhat resembles the plan form shape one would have by taking an axial section through an hourglass. In FIG. 4, however, the front and rear panels are generally triangular, having straight sides 18. Otherwise, the construction of the two is identical. Only the shape of the panel edges is modified between the two embodiments.

The upper portions of the panels are provided with fasteners, which could be simply a pair of fasteners, one on the left and one on the right. Preferably, the fasteners are flexible strips 20 which are fastened to the rear panel at 22, with the other end being loose and covered with an adhesive 24 which bonds to the front panel as shown in FIG. 1. FIG. 1 actually shows a slight modification of the most basic design, which would simply be the strips with the adhesive layer 24. In FIG. 1, it can be seen that a plastic layer 26 comes lying over the adhesive 24 of the fastener strip. This layer 26 is just like any peel-off layer which exposes the underlying adhesive 24, except that the peel-off layer itself has adhesive on the side thereof remote from the fastener strip. Thus, the adhesive on the layer bonds to the front panel of the garment as shown in FIG. 1. The adhesive 24 on the strip 20 bonds to the slick plastic layer 26, but can be peeled off and repositioned on the plastic layer. Because of the slick surface of the layers 26, the adhesive 24 will stick to the plastic, but can be peeled off without ripping the plastic layers 26.

In the embodiments shown, there are two pairs of the strips 20. One pair would also do the job, and of course the strips could be wider, or narrower, or longer or shorter than those shown. The strips would have to have a certain length so that patients of different girths could be accommodated. The exact shape of the upper portions of the panels could be such that the panels would overlap even with persons of substantial girth so that the sticky adhesive 24 would not be in contact with the skin. The garment might also be provided in at least two sizes. Whereas its design would enable one size to fit a range of girths, it might be impractical to use one which would not only fit a very slender person, but a very obese person as well.

It is important to the invention that the strips be in the rib cage area, as shown especially in the upper pair of fastener strips shown in FIG. 1. The garment passes just below the breasts as illustrated in FIG. 1. Any lateral tension would then be felt around the rib cage area, completely removed from the abdominal area where the Caesarean section or other painful incisions would have been made.

Although not essential, ordinarily it would be desirable to have increased absorption in the crotch area of the garment. This could be accomplished by providing a built-in pad which would come with the garment. Ordinarily the pad would be elongated and extend in the dorsal-ventral direction as shown in the drawings.

Alternatively, the crotch of the garment could be provided with a layer of adhesive 28 with a peel-off strip 30 covering it. The strip could be peeled off and then a pad such as indicated at 32 in FIG. 4 could be pressed against the adhesive to hold it in place. This alternative would enable different shaped and sized pads to be utilized. Such design would enable the same garment to be used more effectively for patients having come from different types of operations. The thickness, length, width, and shape of the pad could be varied somewhat to accommodate different operations while retaining the same overall garment.

Thus, the invention fulfills a real humanitarian need for post-operative patients having had the above-indicated types of operations. It fits in well with the increasing movement in medical areas to encounter not only life- and health-threatening situations, but also to provide for the increased comfort and dimensioned pain of the patient so that the psychological trauma is reduced. Instead of just strapping a sanitary napkin belt around the fresh incision of a Caesarean patient and hooking a sanitary napkin onto it, under the theory that the napkin would absorb discharges and the Caesarean incision would heal anyway despite the painful abrasion of the belt, the human need of the patient can now be considered, so that the patient may begin to recuperate in more comfort, with less anxiety, and feeling more protected and covered in the lower abdominal region and thus more at peace throughout the initial time of recuperation from the operation.

I claim:

1. A post operative patient garment comprising:
   (a) a front dimensioned to expand from the crotch area over the abdominal region of the patient up to just beneath the breasts;
   (b) a rear panel defining a continuation of said front panel from the crotch area and dimensioned to extend up the back of the patient;
   (c) fastener means for joining respective upper portions of said panels together above the abdominal region just below the breasts of the patient; and
   (d) an adhesive patch defined on the interior of said garment in the crotch area for bonding an absorptive pad thereto.

2. Structure according to claim 1 wherein said adhesive patch is elongated in the dorsal-to-ventral direction and provided with a peel-off strip.

3. Structure according to claim 2 wherein said garment is provided with an absorptive pad bonded to said adhesive patch in the crotch area.

4. A method of comfortably covering the abdominal and crotch region of a post-operative patient while providing absorptive material for discharges in the crotch area by utilizing a post-operative garment having a crotch area with a peel-off adhesive layer therein, a front panel expanding laterally outwardly from the crotch area, and a back panel which defines a continuation of the front panel in the crotch area and expands laterally upwardly to the back of the patient, and having fastening means to fasten the upper portion of the rear panel to the upper portion of the front panel just below the breasts so that the incision area is not subject to the lateral stress of a belt or other fastener means, comprising the following steps:
   (a) passing said garment through the crotch of the wearer and extending the front panel across the abdominal region up to just below the breasts, and extending the rear panel up along the back of the patient to just below the elevation of the breasts;
   (b) bonding the panels together with the fastening means just below the breasts; and,
   (c) peeling said adhesive layer to expose the adhesive and placing an absorptive pad on said adhesive layer.

* * * * *